(12) United States Patent
Kurrus et al.

(10) Patent No.: US 9,346,181 B2
(45) Date of Patent: May 24, 2016

(54) CATHETER TIP CUTTING TOOL

(71) Applicant: COOK MEDICAL TECHNOLOGIES LLC, Bloomington, IN (US)

(72) Inventors: Michael R. Kurrus, Ellettsville, IN (US); Ram H. Paul, Jr., Bloomington, IN (US); Derek R. Eller, Orient, OH (US); Tyson L. Rugenstein, Camby, IN (US); Christopher B. Crabtree, Bloomington, IN (US); Dennis A. Maddox, Solsberry, IN (US); Jeffry S. Melsheimer, Springville, IN (US); Preston R. Pameijer, Bloomfield, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 179 days.

(21) Appl. No.: 13/974,183

(22) Filed: Aug. 23, 2013

(65) Prior Publication Data

US 2014/0053415 A1   Feb. 27, 2014

Related U.S. Application Data

(60) Provisional application No. 61/693,091, filed on Aug. 24, 2012.

(51) Int. Cl.
*B26D 7/02* (2006.01)
*B26D 5/08* (2006.01)
*A61M 25/00* (2006.01)
*B26B 27/00* (2006.01)

(52) U.S. Cl.
CPC ............ *B26B 27/00* (2013.01); *A61M 25/0009* (2013.01)

(58) Field of Classification Search
CPC .... B26B 27/00; A61M 25/0009; A24F 13/24; Y10T 137/0469; Y10T 83/9444; B26D 3/162
USPC ........ 83/468.8, 597–599, 604, 644, 647, 648, 83/693–694; 30/181, 272.1, 92, 242, 113, 30/494, 94, 182, 184, 186; 604/523
See application file for complete search history.

(56) References Cited

U.S. PATENT DOCUMENTS

| | | | | |
|---|---|---|---|---|
| 1,082,257 | A * | 12/1913 | Davis | 30/113 |
| 1,086,463 | A * | 2/1914 | Robbins | A24F 13/26 30/113 |
| 1,186,291 | A * | 6/1916 | Astruck | 30/112 |
| 2,363,115 | A * | 11/1944 | Brocklebank | 409/206 |
| 3,120,143 | A * | 2/1964 | Kreider | 83/454 |
| 3,728,926 | A * | 4/1973 | Clayton | B26D 3/14 83/468.93 |
| 4,366,619 | A * | 1/1983 | Bieganski | 30/90.1 |
| 4,837,931 | A * | 6/1989 | Beermann | 30/92 |
| 4,872,455 | A * | 10/1989 | Pinchuk et al. | 606/174 |
| 5,105,844 | A * | 4/1992 | King, Sr. | 137/15.14 |
| 5,252,010 | A * | 10/1993 | Obrecht et al. | 408/241 S |
| 5,269,340 | A * | 12/1993 | Drzewiecki | 137/318 |

(Continued)

*Primary Examiner* — Ghassem Alie
*Assistant Examiner* — Bharat C Patel
(74) *Attorney, Agent, or Firm* — Brinks Gilson & Lione

(57) ABSTRACT

A cutting tool is provided for cutting the end of a catheter to provide custom length catheters. The cutting tool has a cutting member that moves within the cutting passageway in the housing. The catheter is positioned within a catheter passageway in the housing. The cutting passageway transacts the catheter passageway so that a blade on the cutting member crosses the catheter passageway and cuts through the width of the catheter to form a cut end on the catheter.

19 Claims, 11 Drawing Sheets

(56) References Cited

U.S. PATENT DOCUMENTS

| | | | | |
|---|---|---|---|---|
| 5,694,691 A | * | 12/1997 | Chen | 30/112 |
| D414,665 S | * | 10/1999 | Longo | D8/60 |
| 5,992,022 A | * | 11/1999 | Carrera Moya | A24F 13/24 |
| | | | | 131/248 |
| 6,041,810 A | * | 3/2000 | Dudley | 137/318 |
| 6,164,286 A | * | 12/2000 | Schad | 131/248 |
| 6,223,637 B1 | | 5/2001 | Hansen | |
| 6,295,991 B1 | * | 10/2001 | Emery | 131/250 |
| 8,006,594 B2 | | 8/2011 | Hayner et al. | |
| 8,695,608 B2 | * | 4/2014 | Bardelli | 131/250 |
| 2006/0249166 A1 | * | 11/2006 | Lauzon | 131/248 |
| 2008/0236358 A1 | * | 10/2008 | Vitullo et al. | 83/663 |
| 2009/0265941 A1 | | 10/2009 | Kurrus | |
| 2011/0302785 A1 | * | 12/2011 | Chuan | 30/113 |

* cited by examiner

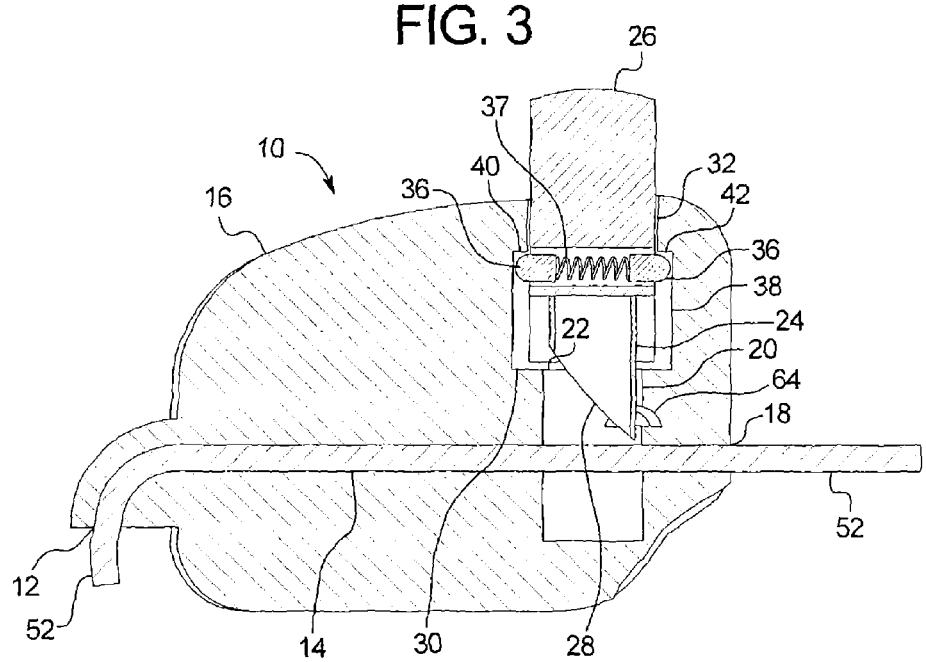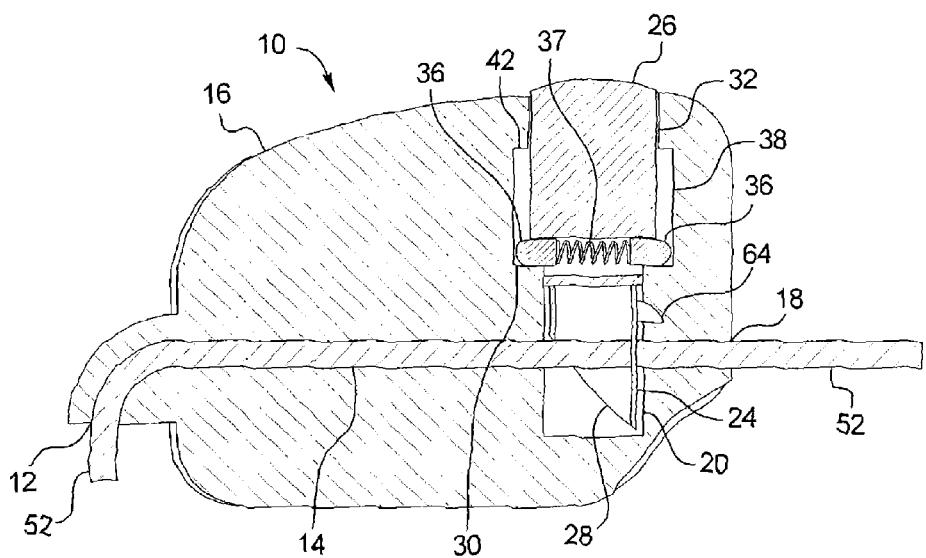

FIG. 10
FIG. 11
FIG. 12
FIG. 13
FIG. 15
FIG. 14
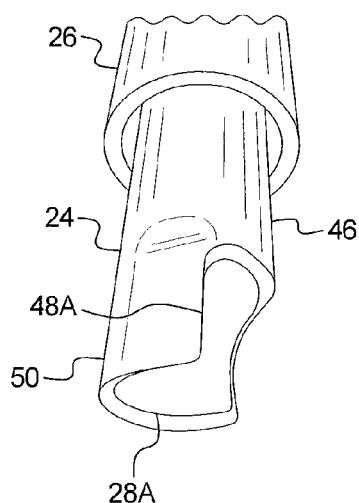
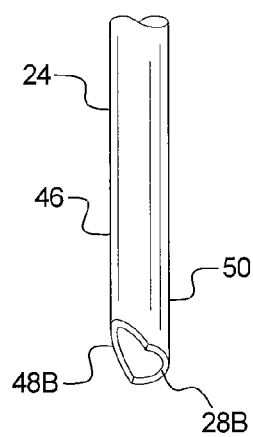
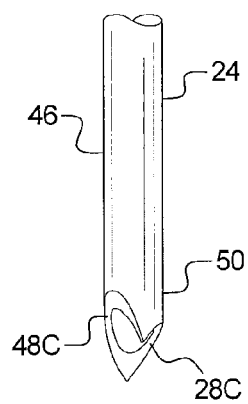
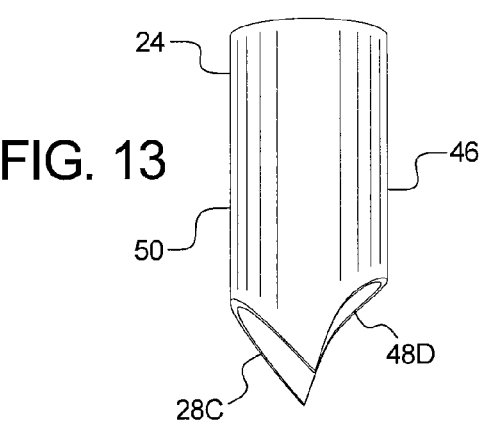
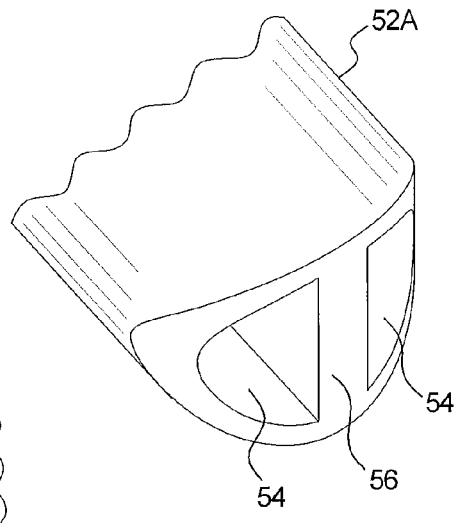
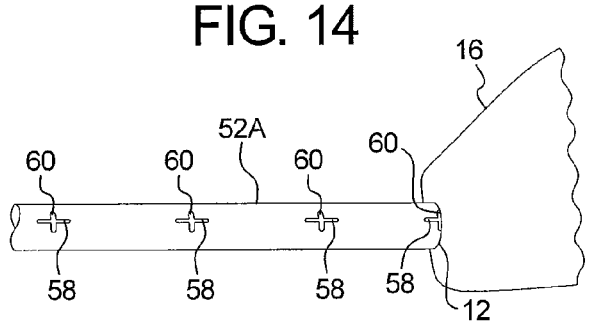

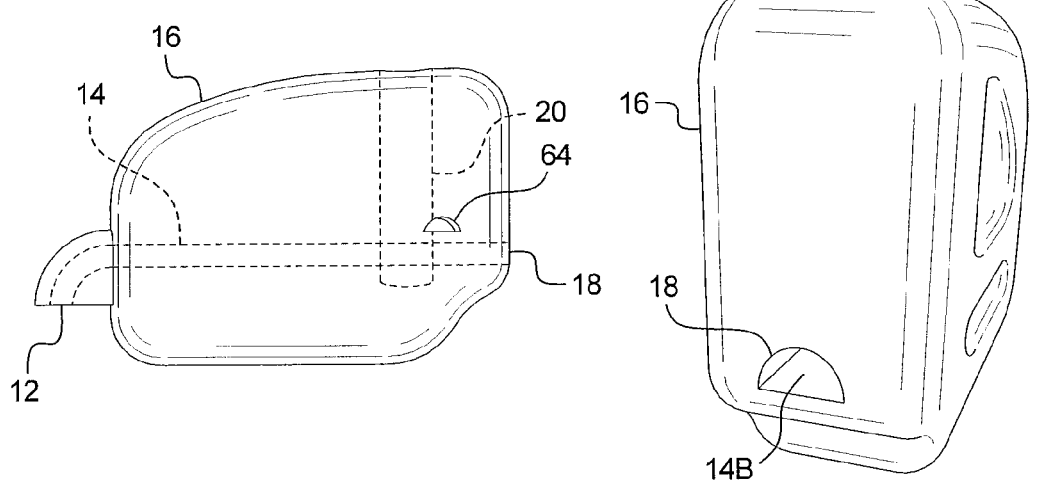
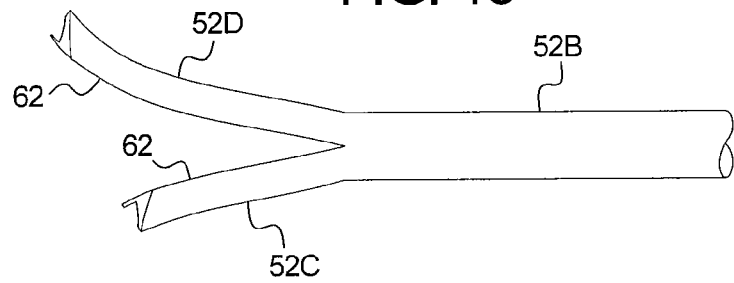
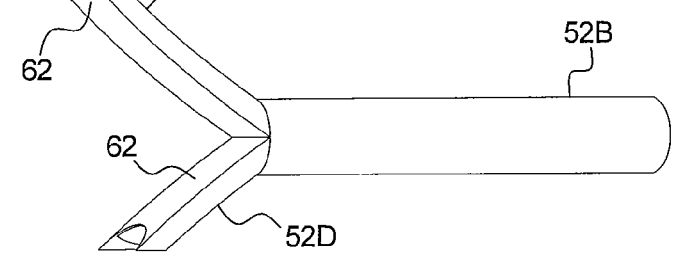

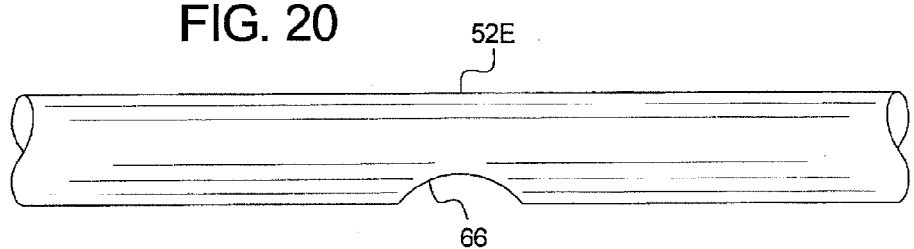
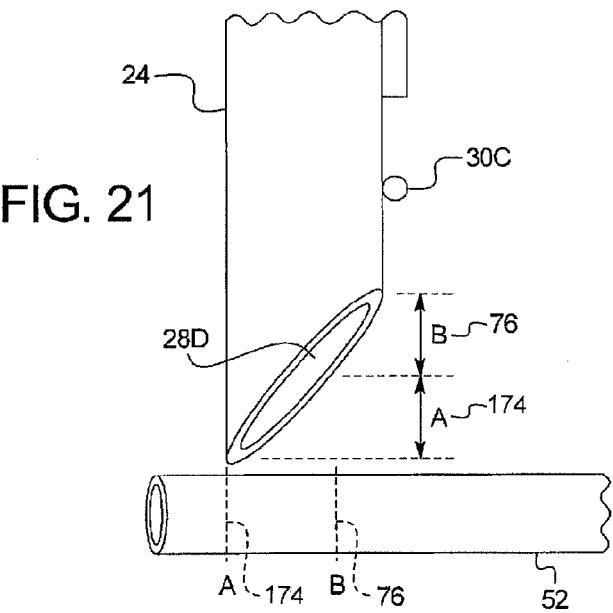
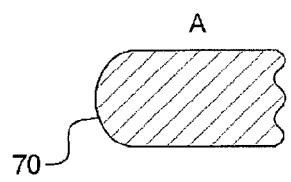 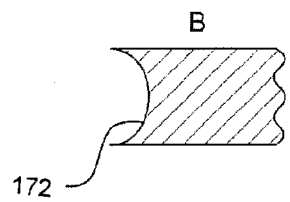

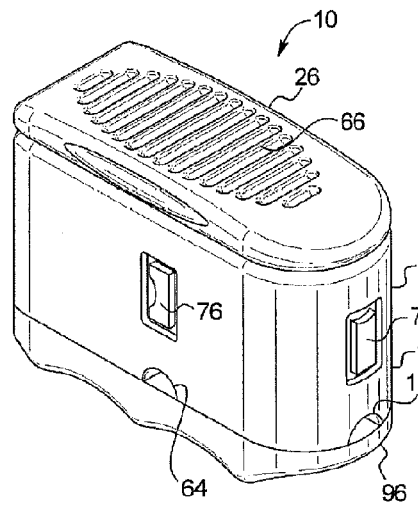
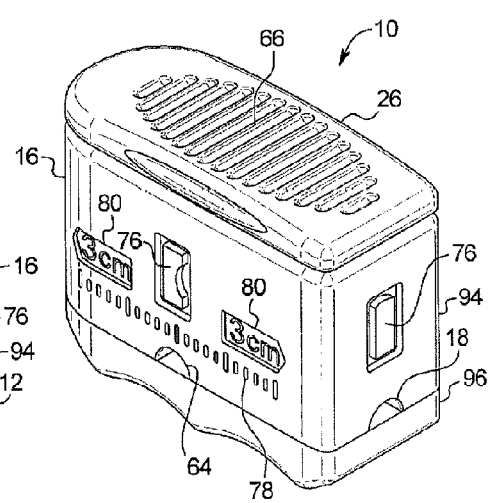
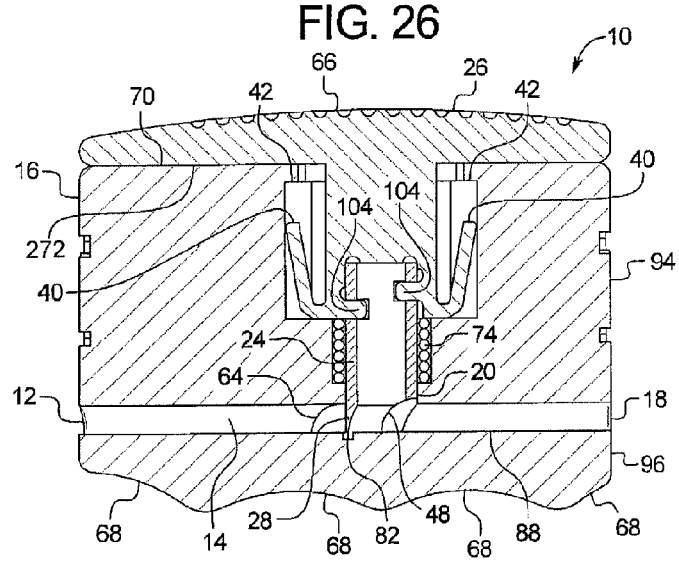

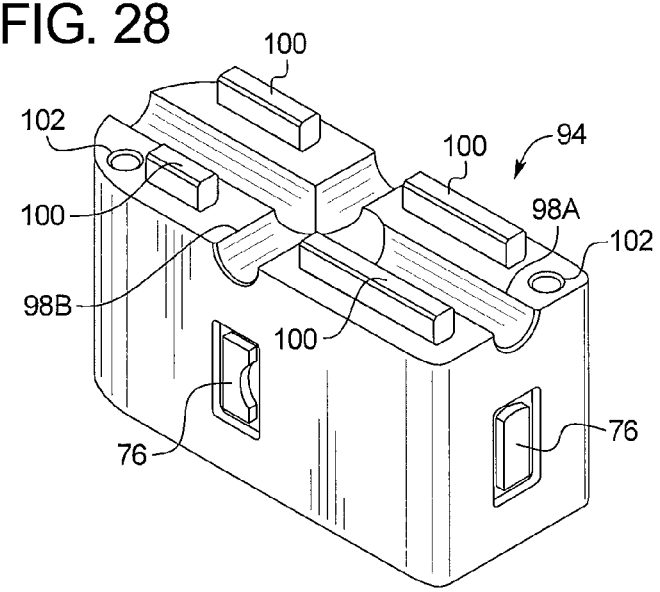
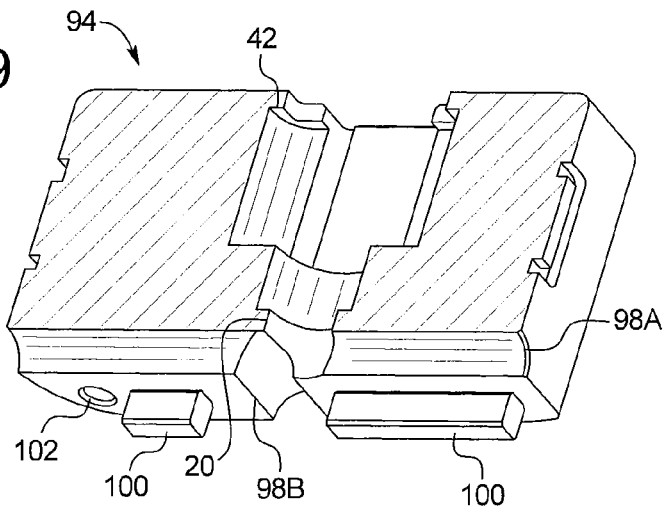
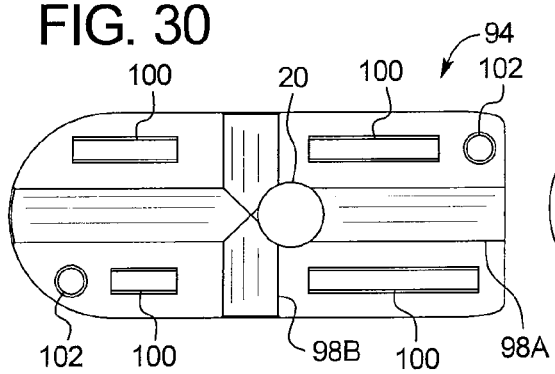
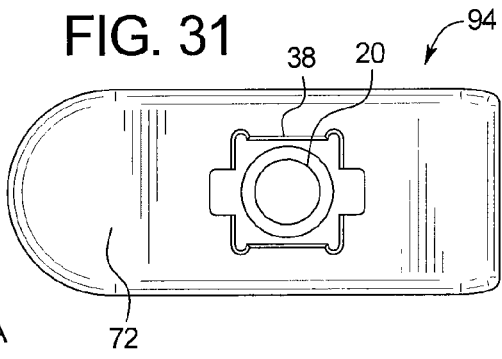

CATHETER TIP CUTTING TOOL

This application claims priority to U.S. Provisional Application No. 61/693,091, filed Aug. 24, 2012, which is hereby incorporated by reference herein.

BACKGROUND

The present invention relates generally to medical devices and more particularly to a device for cutting the end of a catheter.

Minimally invasive medical procedures have become common in the medical profession due to the lower risk and trauma associated with minimally invasive procedures and the lower cost compared to open surgical procedures. Minimally invasive procedures generally involve gaining access to an internal region of a patient like a vessel by puncturing the patient's skin, the intermediate tissues between the skin and the vessel, and the wall of the vessel. An elongate medical instrument may then be inserted through the access site so that the distal end of the medical instrument is located within the patient's internal vessel, while the proximal end of the medical instrument remains outside the patient's body. The physician may then manipulate the proximal end of the medical instrument outside the patient's body to move and orient the distal end of the medical instrument to a location within the vessel where treatment is desired. Thus, a treatment site within a patient's vessel may be treated from outside the patient's body through a relatively small access site that is located some distance from the treatment site. By contrast, conventional open surgical procedures would require opening the tissues immediately adjacent the treatment site so that the surgeon can gain direct access to the treatment site.

One type of medical instrument used in minimally invasive procedures is a catheter. Generally, a catheter is any type of elongate tubular device that is designed to extend into a patient's body through an access site. Catheters are used for numerous purposes, such as infusing drugs or nutrients into a patient's body, withdrawing bodily fluids from a patient's body, and delivering various types of devices to a treatment site within a patient's body, etc.

While many catheters are designed to be used by a physician in the state the catheter was originally manufactured by the manufacturer without any modifications, some catheters commonly require special customization by the physician to suit the particular use or patient that the catheter is being used for. For example, peripherally inserted central catheters ("PICC") are often cut to length by a physician or the physician's staff so that the distal end of the catheter will be positioned at a specific location in the patient's body. This is typically done by cutting off a portion of the distal end of the catheter as it is provided by the manufacturer with a razor or scissors to shorten the length of the catheter to the overall length that is desired. However, this type trimming usually results in a blunt end that can present sharp edges that may scrape and traumatize the internal tissues within the patient's body. Alternatively, where the physician attempts to manually trim an atraumatic end on the catheter, such cuts are typically non-uniform and/or roughly cut due to the difficulty of manually cutting a non-straight end. Also, some cutting tools like scissors may leave a rough end surface that may encourage the accumulation of blood clots or bacteria.

Accordingly, the inventors believe that it would be desirable to provide a cutting tool that a physician or the physician's staff could use to customize the distal end of a catheter with an atraumatic end.

SUMMARY

A cutting tool is described for cutting standard catheters in a medical setting to customize the length of the catheter for particular patients and uses. The cutting tool forms an arc-shaped end on the catheter with a single cut in one direction. Thus, the end is atraumatic and has a smooth cut end. The cutting tool has a cutting member that moves through a cutting passageway. The cutting passageway transects a catheter passageway. The cutting member has a blade at the bottom end that cuts through the entire width of the catheter to cut a remnant loose from the catheter to shorten the length of a standard catheter. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 3 is a cross-sectional view of another catheter cutting tool, showing the cutting member at the top of a cutting stroke;

FIG. 4 is a cross-sectional view of the catheter cutting tool of FIG. 3, showing the cutting member at the bottom of the cutting stroke;

FIG. 10 is a perspective view of a cutting member;

FIG. 11 is a perspective view of another cutting member;

FIG. 12 is a perspective view of another cutting member;

FIG. 13 is a perspective view of another cutting member;

FIG. 14 is a top view of a catheter extending through the cutting tool, showing marks for visual alignment;

FIG. 15 is an end perspective view of a dual lumen catheter;

FIG. 16 is a side view of the housing;

FIG. 17 is an end perspective view of the catheter cutting tool, showing a D-shaped second opening of the catheter passageway;

FIG. 18 is a side view of a hemodialysis catheter;

FIG. 19 is a perspective view of another hemodialysis catheter;

FIG. 20 is a top view of a side port;

FIG. 21 is a side view of a cutting member and a catheter, showing two depths of cut;

FIG. 22 is a top view of convex-shaped end on a catheter;

FIG. 23 is a top view of concave-shaped end on a catheter;

FIG. 24 is a side perspective view of another embodiment of the cutting tool;

FIG. 25 is another side perspective view of the cutting tool;

FIG. 26 is a cross-sectional view of the cutting tool;

FIG. 28 is a bottom perspective view of the first housing;

FIG. 29 is a cross-sectional perspective view of the first housing;

FIG. 30 is a bottom view of the first housing;

FIG. 31 is a top view of the first housing;

DETAILED DESCRIPTION

Figure 5:
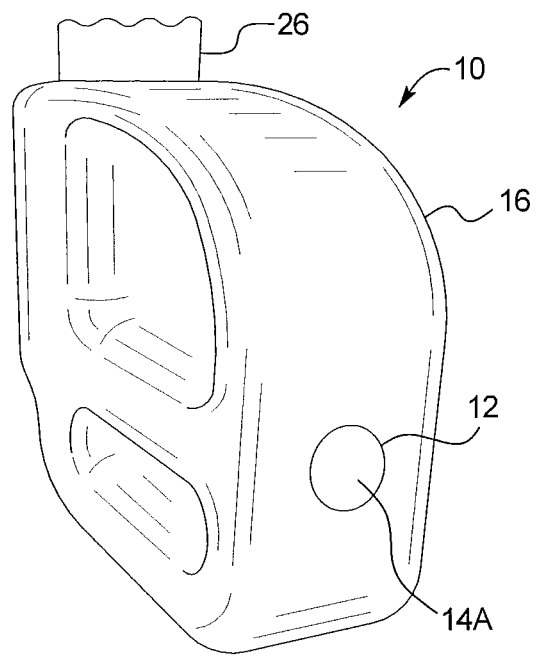
FIG. 5 is an end perspective view of the catheter cutting tool, showing the first opening of the catheter passageway.
Figure 6:
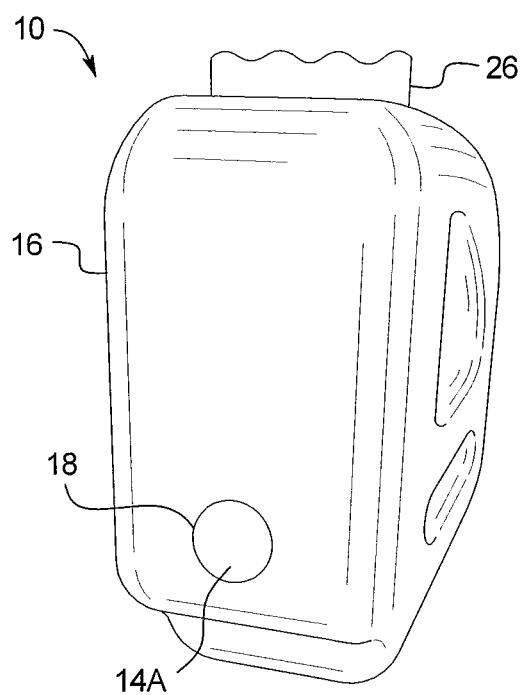
FIG. 6 is an end perspective view of the catheter cutting tool, showing the second opening of the catheter passageway.

Referring now to the figures, and particularly to FIGS. 1-6, a catheter cutting tool 10 is shown. The cutting tool 10 is designed to be used by a physician or the physician's staff to customize a catheter 52 that is provided by a manufacturer. Thus, for example, the cutting tool 10 could be used in a hospital setting to trim the length of a standard catheter 52 to a custom length that is intended to specifically fit an individual patient. To use the cutting tool 10, the operator pushes the distal end of a catheter 52 through a first opening 12 of a catheter passageway 14 that extends through a housing 16. Preferably, the passageway 14 also has a second opening 18 so that the distal end of the catheter 52 can exit the opposite side of the housing 16 as far as necessary to cut the catheter 52 at the desired length. The cross-sectional shape of the passageway 14 is preferably the same as the catheter body 52 and is preferably sized to provide a moderate to minimal slip fit with the body 52 of the catheter 52. For example, as shown in FIGS. 5-6, the first and second openings 12, 18 and catheter passageway 14A may have a round cross-sectional shape adapted for a round catheter body 52.

The housing 16 also includes a cutting passageway 20 that transects the catheter passageway 14. The cutting passageway 20 has an opening 22 that a cutting member 24 extends through. Although the cutting passageway 20 may have a second opening so that the passageway 20 extends all the way through the housing 16, it is preferable for the cutting passageway 20 to extend only partially through the housing 16 so that the cutting member 24 is fully enclosed within the cutting passageway 20. The cross-sectional shape of the passageway 20 is preferably the same as the cutting member 24 and is preferably sized to provide a moderate to minimal slip fit with the cutting member 24.

Figure 8:
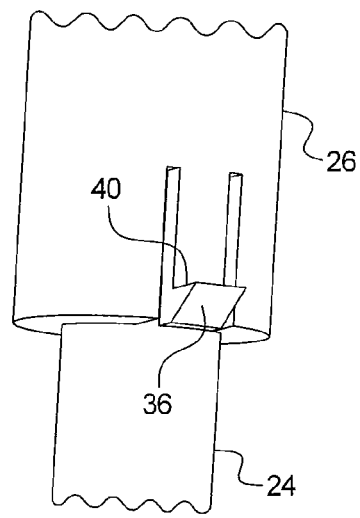
FIG. 8 is an enlarged view of the knob and cutting member, showing a catch.
Figure 9:
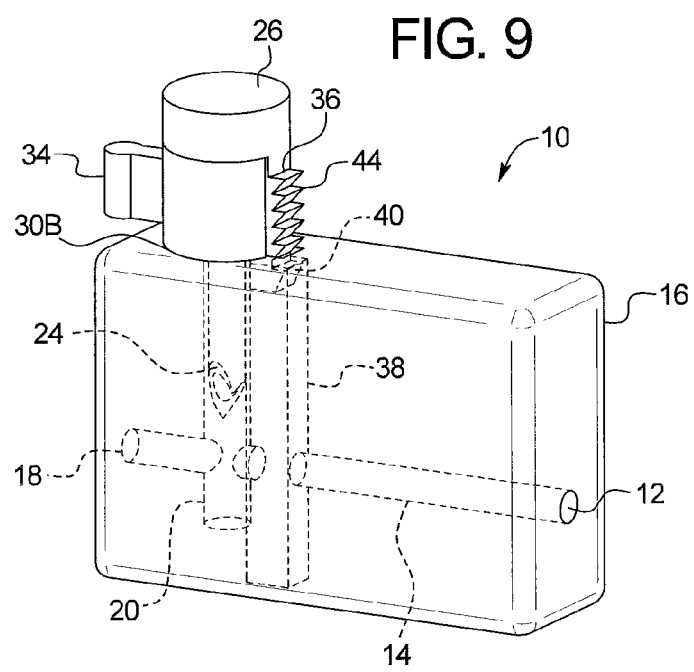
FIG. 9 is a perspective view of another catheter cutting tool.

As shown in FIGS. 1-4, the cutting member 24 may be provided with a knob 26 at the top end that may be pressed by an operator's finger or hand. The knob 26 is preferably larger in size than the cutting member 24 to make the knob 26 comfortable to push and may be larger in size than the cutting passageway 20. Thus, the length of the cutting member 24 and the position of the catheter passageway 14 can be designed so that the knob 26 stops the travel of the cutting member 24 when the blade 28 crosses the catheter passageway 14 by contacting a stop surface 30 on the housing 16. For example, in FIG. 7, the stop surface 30A is within the housing 16 at the bottom of a passageway 32 through which the knob 26 slides. Alternatively, as shown in FIG. 9, the stop surface 30B may be the top surface 30B of the housing 16. As shown in FIG. 9, the cutting tool 10 may also be provided with a locking member 34 to prevent the cutting member 24 from crossing the catheter passageway 14 until the locking member 34 is removed. The locking member 34 may be positioned between the knob 26 and the housing 16 to prevent the knob 26 from being pushed. Preferably, the locking member 34 has a slot that slides around the cutting member 24 and is sized to abut the bottom of the knob 26 and the top of the housing 16. Thus, the locking member 34 is removable by sliding the locking member 34 away from the cutting member 24 through the slot. Alternatively, in the embodiments of FIGS. 1-8, the cutting tool 10 need not be provided with a locking member, or the locking member may take another form such as a detent or the like.

Figure 7:
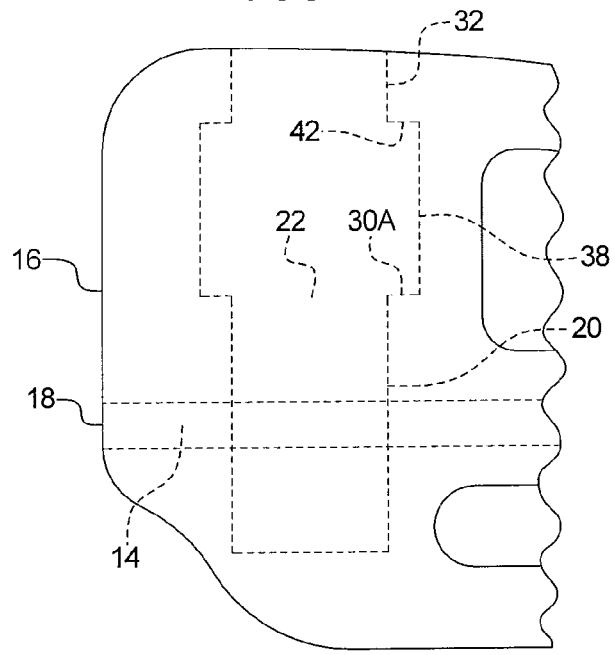
FIG. 7 is an enlarged side view of the housing, showing the cutting passageway and catheter passageway.

The cutting tool 10 preferably has a guide 36 that prevents the cutting member 24 from rotating in the cutting passageway 20. This is especially useful where the cutting member 24 has a round cross-section. As shown in FIGS. 7-8, the guide 36 is attached to the cutting member 24 and extends through a guide passageway 38. The guide passageway 38 extends through the housing 16 generally parallel to the cutting passageway 20 so that the guide 36 moves through the guide passageway 38 as the cutting member 24 moves through the cutting passageway 20. As shown, the guide 36 may be connected to the cutting member 24 by being attached to the knob 26, which is attached to the cutting member 24. Thus, the guide 36 need not be directly attached to the side surface of the cutting member 24, and there may be a lateral space between the guide 36 and the cutting member 24 that separates the guide 36 and cutting member 24 from each other along their lengths.

The guide 36 may also be provided with a catch 40 that engages a catch 42 in the housing 16. The catches 40, 42 engage each other when the cutting member 24 is at the top of its stroke to prevent the cutting member 24 from being removed from the cutting passageway 20. As shown in FIG. 9, the guide 36 and/or housing 16 may be provided with a plurality of catches 44 that engage as the cutting member 24 is pushed through the cutting passageway 20. In this design, it is preferable for the guide 36 to be flexible and the guide passageway 38 to have enough space to allow the guide 36 to flex so that the catches 44 can pass over the housing catch 42 as the guide 36 and cutting member 24 move downward. Multiple catches 44 like this would be desirable if the cutting tool 10 is intended to be used for a single cut, and it is desired to prevent the cutting member 24 from being raised after the blade 28 crosses the catheter passageway 14. However, it may be preferable to provide single catches 40, 42 at the bottom of the guide 36 and the top of the guide passageway 38 to allow the cutting member 24 to be moved back to the top of the stroke after the catheter 52 has been cut so that the cutting tool 10 may perform multiple cuts.

As shown in FIGS. 3-4, the catch 40 may also be a plunger 40 that is biased outward into the guide passageway 38 by a spring 37. If desired, the catch 40 may also stop the travel of the cutting member 24 by contacting the stop surface 30 at the bottom of the cutting stroke. Detent recesses could also be provided within the guide passageways 38 at the top of the cutting stroke in order to provide initial resistance when pressing down on the knob 26. Although the cutting tool 10 of FIGS. 3-4 may be used with any of the cutting members 24 shown in FIGS. 10-13, the cutting member 24 may also have a single beveled blade 28 like FIG. 21. In order to produce convex-shaped cuts through the catheter 52, it is preferable for the downward travel of the cutting member to be limited so that only one side of the blade 28 fully cuts through the catheter, while the other side of the cutting member 28 is prevented from crossing the catheter passageway 14.

Figure 1:
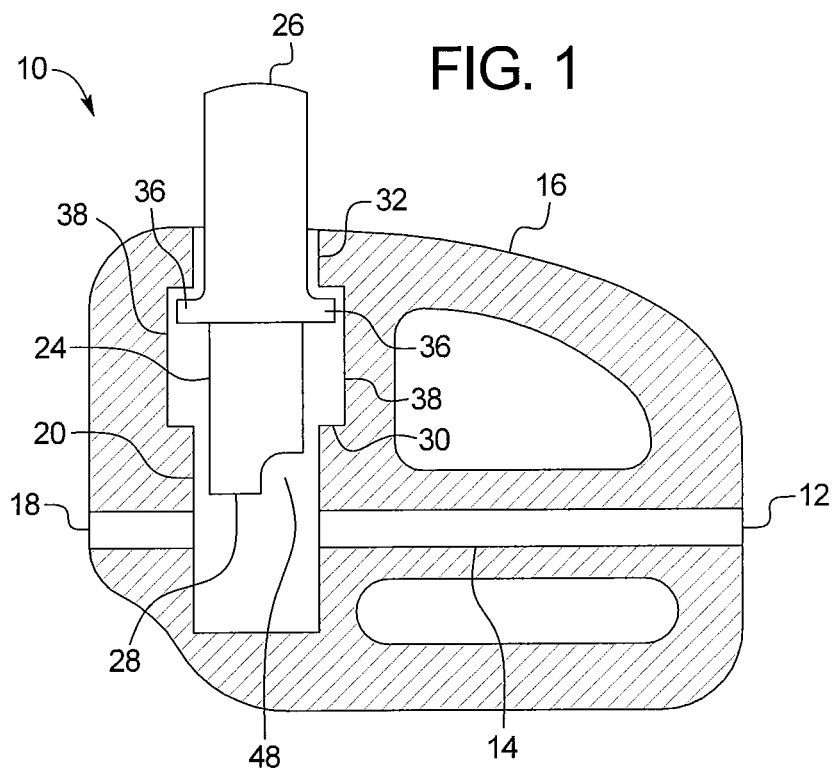
FIG. 1 is a cross-sectional view of a catheter cutting tool, showing the cutting member at the top of a cutting stroke.
Figure 2:
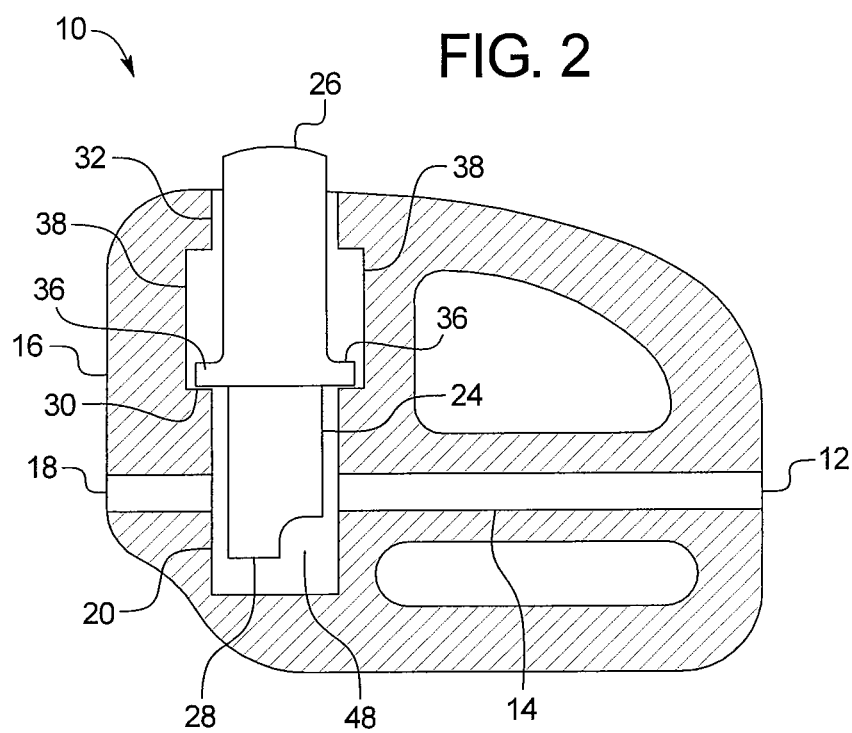
FIG. 2 is a cross-sectional view of the catheter cutting tool, showing the cutting member at the bottom of the cutting stroke.

As shown in FIGS. 8-13, the cutting member 24 preferably is a hollow tube 24 with a sharp blade 28 at the bottom end. Thus, the blade 28 is defined by at least part of the circumference of the hollow tube 24. The blade 28 may be at least as wide as the catheter passageway 14 and catheter body 52 or wider, and may be arc-shaped. Therefore, when the cutting member 24 is pushed through the cutting passageway 20 so that the blade 28 crosses the catheter passageway 14 as shown in FIG. 2, the blade 28 cuts through the catheter body 52 and forms an arc-shaped distal end on the catheter body 52 in the shape of the blade 28. As a result, the operator is able to easily form an atraumatic distal end on a catheter 52 by positioning the catheter body 52 in the catheter passageway 14 until the desired distal end location is aligned with the cutting passageway 20 and blade 28, and pushing the cutting member 24 with a finger or hand. This forms an arc-shaped distal end with a single cut of the blade 28 moving in one direction and forms a smooth cut surface at the very end of the catheter 52.

In a preferred embodiment, the cutting member 24 is hollow with a generally round cross-section, and the cutting passageway 20 has a corresponding generally round cross-section. Thus, where the cutting passageway 20 is centered with the catheter passageway 14, the blade 28 forms a symmetrical convex-shaped end on the catheter body 52, with the distal-most point of the end being at the center of the catheter 52. However, it is also possible that the blade 28 could have a non-round convex-shape if desired. Further, as described below, the cutting passageway 20 could be off-center from the catheter passageway 14 to form an arc-shaped distal end that is asymmetrical.

Where the cutting member 24 is a hollow tube 24, it is preferable for the side 46 of the cutting member 24 that is closest to the first opening 12 to be relieved 48 at the blade 28 end so that the first side 46 of the tube 24 does not contact the catheter body 52 when the blade 28 crosses the catheter passageway 14. Thus, while the first side 46 of the cutting member 24 is located in the direction of and closer to the proximal end of the catheter body 52 than the second side 50, the first side 46 is not the side of the cutting member 24 that cuts through the catheter body 52. Instead, the blade 28 is preferably on the second side 50 of the cutting member 24 that is closest to the second opening 18 and located in the direction of the remnant of the catheter body 52 that is cut loose by the cutting tool 10. This results in a convex-shaped cut when the catheter 52 is fed through the first opening 12 of the housing 16.

As shown in FIG. 10, the blade 28 may have a straight, blunt end 28A on the side 50 opposite from the relief 48A. This will result in the blade 28A contacting and cutting through the middle of the catheter body 52 first if the catheter 52 is round, since the middle of the catheter body 52 will be higher than the opposing outer regions. Further, in FIG. 10, the generally round cross-sectional shape of the blade 28A is oblong. Alternatively, as shown in FIG. 11, the generally round cross-sectional shape of the blade 28B may be circular. Also, the relief 48B may be a beveled edge 48B. As shown in FIG. 12, the blade 28C may also be relieved so that the center of the blade 28C is higher than the outer regions of the blade 28C. For example, the blade 28C may be beveled with a beveled shape that is lower than the relief 48C so that the beveled blade 28C cuts through the catheter 52 but the relief 48C does not cut through the catheter 52. This design could be used to alter what part of the catheter 52 is cut first and what portion of the blade 28C cuts simultaneously through the top wall of the catheter body 52. For example, the center of the blade 28C could be sufficiently higher than the outer regions of the blade 28C so that the outer regions cut through the top wall of the catheter body 52 first before the center of the blade 28C. Alternatively, the center of the blade 28C and the outer regions of the blade 28C could be shaped so that substantially the entire width of the blade 28C cuts through the top wall of the catheter body 52 at substantially the same time. As shown in FIG. 13, the blade 28C may be a straight bevel like FIG. 12, and the relief 48D may have an inwardly curved bevel shape.

The cutting tool 10 may also be used with a specially marked catheter 52A to radially orient the catheter body 52A relative to the cutting blade 28. As shown in FIG. 15, this may be particularly useful for cutting a dual lumen catheter 52A with side-by-side lumens 54 separated from each other by a septum 56. For example, as shown in FIG. 15, it may be preferable for the cut end of the catheter 52A and the blade 28 to be convex-shaped with the center of the blade 28 cutting along the width of septum 56. Thus, the end of the septum 56 extends to the distal-most end of the catheter 52A and is smoothly and uniformly cut along its width by the blade 28. As shown in FIG. 14, this may be accomplished by providing a mark 58 on the exterior of the catheter body 52A that is aligned with the length of the septum 56. This allows the operator to visually align the catheter body 52A and septum 56 relative to the cutting blade 28 by orienting the mark 58 upright so that the blade 28 cuts down along the septum 56. The catheter body 52A may also be provided with multiple marks 58, 60 along its length, where each mark 58, 60 combines two marks 58, 60 identifying two different positional orientations. For example, each mark 58, 60 may have a longitudinal mark 58 identifying the orientation of the septum 56 and a lateral mark 60 identifying a particular cut length. Thus, an operator may use the marks 58, 60 both to position the catheter 52A relative to the housing 16 for a specific cut length that is desired, and to radially align the septum 56 relative to the cutting blade 28.

As shown in FIGS. 3-4 and 16, the first opening 12 and the second opening 18 of the catheter passageway 14 may be positioned out of alignment with each other so that the catheter passageway 14 does not extend straight through the housing 16. For example, the first and second openings 12, 18 may be oriented about 90° from each other. As a result, the catheter 52 is bent along the catheter passageway 14 and is frictionally restrained in the passageway 14. This may be helpful to allow the cutting tool 10 to be used without needing to constantly hold the catheter 52 during the cutting step. Thus, the catheter body 52 could be pushed through the catheter passageway 14 to the desired cutting position, and then the operator could let go of the catheter 52. Because of the frictional restraint between the catheter passageway 14 and the catheter body 52, the catheter 52 tends to retain its position even without the operator holding the catheter 52. The operator may then hold the housing 16 with one hand while pushing the knob 26 with the other hand to cut the catheter 52. The catheter passageway 14 may be straight from the first opening 12 to the cutting passageway 20, and may be curved between the cutting passageway 20 and the second opening 18. Thus, the portion of the catheter body 52 that will form the end of the trimmed catheter 52 is not bent by the catheter passageway 14, but the remnant that is cut loose is bent to frictionally restrain the catheter 52. Alternatively, as shown in FIGS. 3-4 and 16, the catheter passageway 14 may be curved between the first opening 12 and the cutting passageway 14 and may be straight from the cutting passageway 14 to the second opening 18. In this design, the catheter 52 remains frictionally restrained throughout the cutting process, and the remnant can freely slide out of the catheter passageway 14.

As shown in FIGS. 17-19, the cutting tool 10 may also be used to cut catheters 52B with a D-shaped cross-section by providing a D-shaped catheter passageway 14B and D-shaped first and second openings 12, 18. This may be particularly useful for hemodialysis catheters 52B where the catheter 52B has two D-shaped catheter bodies 52C, 52D, that when put together along the flat sides 62 form a generally rounded or oval outer circumference. Thus, in a hemodialysis catheter 52B with two D-shaped catheter bodies 52C, 52D, each of the D-shaped catheter bodies 52C, 52D may be cut independently of each other so that each of the bodies 52C, 52D can have a different length. Therefore, in order to cut the second body 52D after the first body 52C has been cut, the catheter 52B may be rotated 180° to line up the D-shaped cross-section of the second body 52D with the catheter passageway 14B. Thus, a single cutting tool 10 can be used to cut both of the D-shaped bodies 52C, 52D. As shown in FIGS. 18-19, it may be desirable to cut the first catheter body 52C longer and the second catheter body 52D shorter. As shown in FIG. 19, it may also be desirable to cut the shorter, second catheter body 52D with a concave-shaped end instead of a convex-shaped end like the longer, first catheter body 52C. This may be achieved by pushing the distal end of the second catheter body 52D through the second opening 18 of the housing 16 instead of the first opening 12 so that the blade 28 makes a reverse cut instead of the convex cut described above.

As shown in FIGS. 2-3 and 16, the housing may also be provided with a second catheter passageway 64 for skiving, or cutting, a side port 66 in the catheter 52E. The second catheter passageway 64 is preferably sized to provide a moderate to minimal slip fit with the body 52E of the catheter 52E. Preferably, the second catheter passageway 64 is oriented perpendicularly to the first catheter passageway 14 and only partially transects the cutting passageway 20. Thus, as shown in FIG. 20, the second catheter passageway 64 may be positioned so that the blade 28 of the cutting member 24 cuts through the side of the catheter 52E without cutting through the full width of the catheter 52E. Therefore, by having two different catheter passageways 14, 64, the cutting tool 10 may be used to cut atraumatic ends on catheters 52E and side ports 66 in catheters 52E with the same cutting member 24.

As shown in FIGS. 21-23, the cutting tool 10 may also be provided with a cutting member 24 and stop 30C that is capable of cutting both convex and concave ends 70, 172 with the catheter 52 extending in the same direction. In this design, the cutting member 24 may be a hollow tube 24 with a beveled blade 28D that is beveled in a single direction along the full circumference of the tube 24. The cutting member 24 may be allowed to travel along a first depth of cut 174 until the cutting member 24 reaches the stop 30O, which prevents the cutting member 24 from traveling along a second depth of cut 76. The first depth of cut 174 is designed to cut through the catheter 52 with a lower portion of the beveled blade 28D, which cuts a convex-shaped end 70 on the catheter 52 as shown in FIG. 22. Thus, in this state, the upper portion of the beveled blade 28D is prevented from cutting through the catheter 52 by the stop 30C. When it is desired to use the cutting tool 10 to cut a concave-shaped end 172 on a catheter 52, the stop 30C may be removed to allow the cutting member 24 to move along the second depth of cut 76. The second depth of cut 76 is designed to cut through the catheter 52 with the upper portion of the beveled blade 28D, which cuts a concave-shaped end 172 on the catheter 52 as shown in FIG. 23. Alternatively, the cutting members 24 shown in FIGS. 10-13 with blades 28, 48 facing in two directions could be used with two different depths of cut 174, 76 and a removable stop 30C to cut convex and concave ends 70, 172.

Another embodiment of the cutting tool 10 is shown in FIGS. 24-36. A number of the features of the cutting tool 10 shown in FIGS. 24-36 are the same or similar to the features already described above, and therefore, the entire description provided above need not be repeated for an understanding of FIGS. 24-36. As shown in FIGS. 24-36, the cutting tool 10 may have a first opening 12, catheter passageway 14, housing 16, second opening 18, cutting passageway 20, cutting member 24, knob 26, blade 28, guide 36, guide passageway 38 (or knob passageway), catches 40, 42, relief 48, and second catheter passageway 64.

Figure 36:
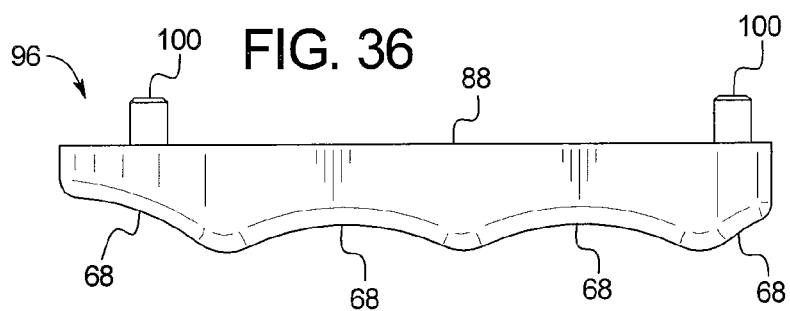
FIG. 36 is a side view of the second housing.

As shown in FIGS. 24-27, the knob 26 may have a top surface 66 that is generally the same shape as the housing 16 so that the knob 26 generally covers the top of the housing 16. As also shown in FIG. 36, the bottom of the housing 16 may be provided with finger recesses 68. Thus, the cutting tool 10 may be operated by wrapping the user's fingers around the bottom of the housing 16 and resting the knob 26 in the user's palm. The cutting tool 10 may then be squeezed by the user to push the knob 26 down against the housing 16 with the user's palm to cut the catheter extending through the catheter passageway 14.

In FIGS. 24-26, the knob 26 is shown pressed down with the cutting member 24 being pushed through the catheter passageway 14. In this embodiment, the bottom surface 70 of the knob 26 may contact the top surface 72 of the housing 16 to define a stop 272 for the end of the travel of the cutting member 24. A spring 74 may also be provided within the housing 16 to bias the knob 26 and the cutting member 24 away from the catheter passageway 14. Preferably, the spring 74 surrounds the cutting member 24 as shown in FIG. 26. A flexible catch 40 on the knob 26 allows the knob 26 to be inserted into the housing 16 during assembly but prevents the knob 26 from being removed from the housing 16 after assembly. Thus, as the spring 74 biases the knob 26 upward, the catch 40 on the knob 26 contacts the catch 42 on the housing 16 to stop upward travel of the knob 26 and the cutting member 24. Although the embodiments in the figures generally show a knob 26 that is pressed straight down to actuate the cutting member 24, it should be understood that other types of knob 26 like pivoting levers, etc. could also be used to actuate the cutting member 24.

As shown in FIGS. 24-25, indicator 76 may be provided next to the first opening 12, second opening 18, and second catheter passageway 64 to illustrate to the user the shape of cut that will occur if the catheter is inserted through each respective opening. The side of the housing 16 may also be provided with measurement markers 78 that indicate a length from the cutting blade 28. For example, a label 80 may be provided for the length from each opening 12, 18 to the cutting blade 28 so that the user can estimate from the end of the housing 16 where the catheter will be cut. If desired, the housing 16 may also be made transparent so that the user can see inside the housing 16 to see where the blade 28 is located and where the catheter will actually be cut.

Figure 27:
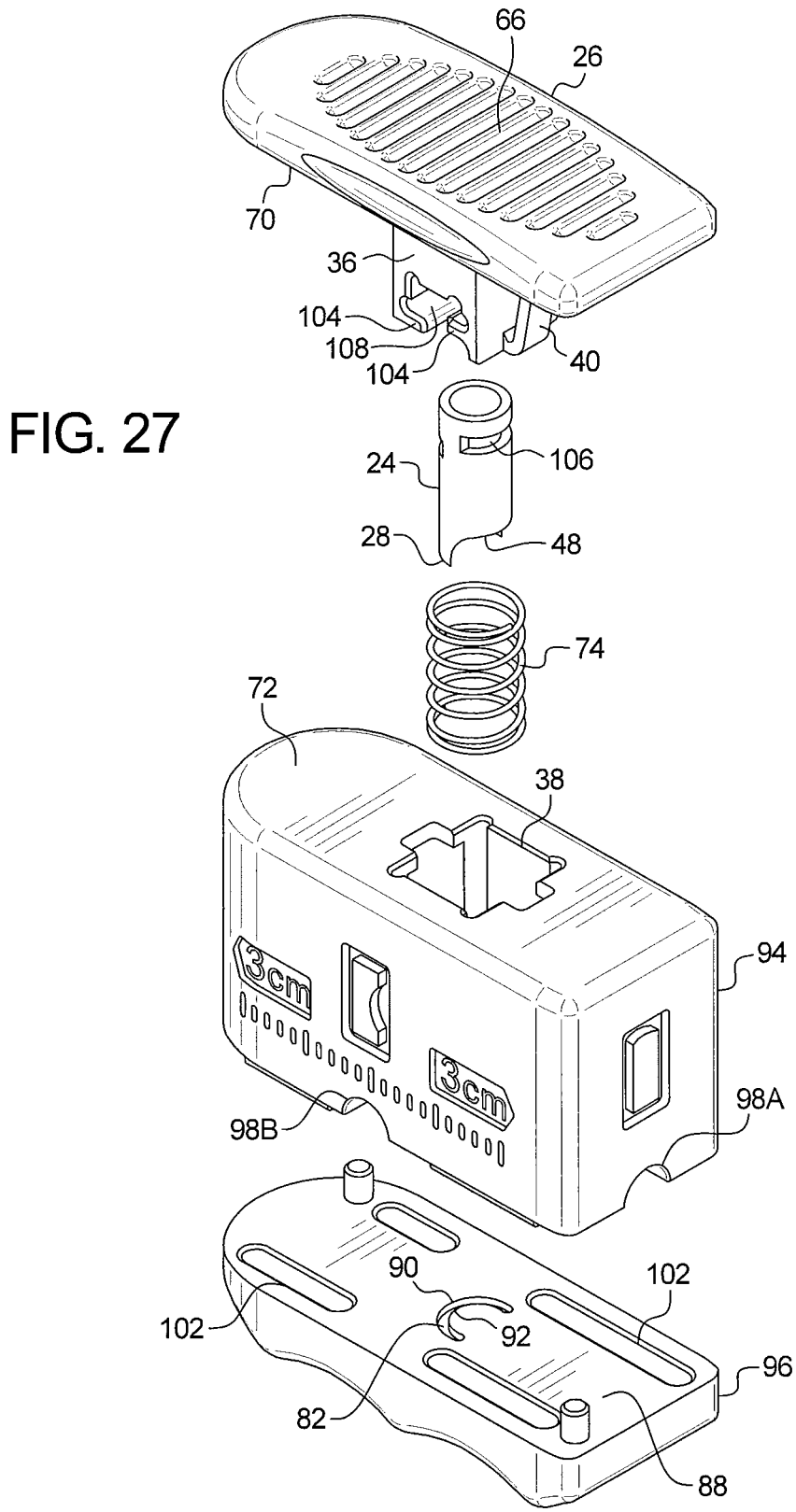
FIG. 27 is an exploded view of the cutting tool.
Figure 32:
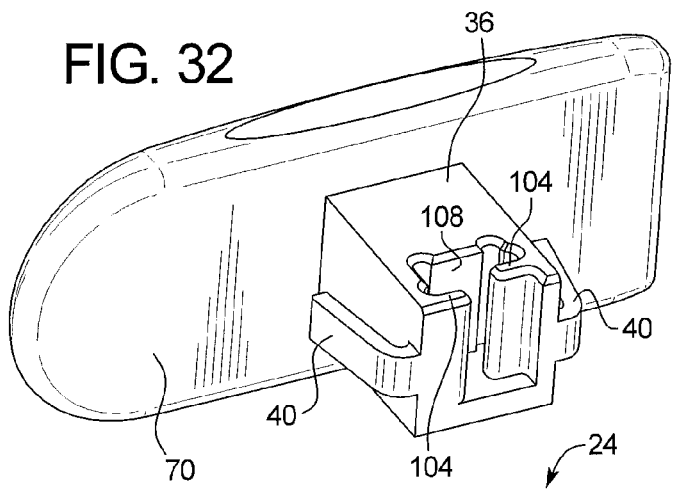
FIG. 32 is a bottom perspective view of the knob.
Figure 33:
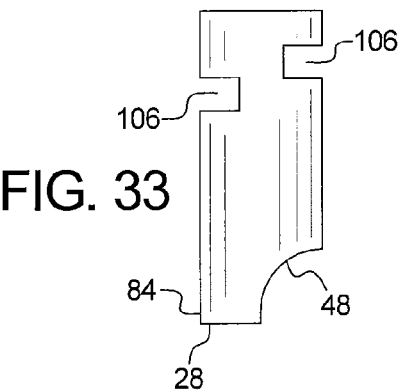
FIG. 33 is a side view of the cutting member.
Figure 34:
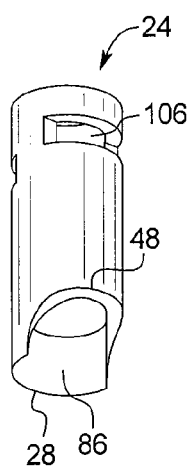
FIG. 34 is a perspective view of the cutting member.

As shown in FIG. 27, the guide 36 which prevents the cutting member 24 from rotating inside the housing 16 may be a square portion 36 of the knob 26 that slides through a square knob passageway 38 in the housing 16.

Figure 35:
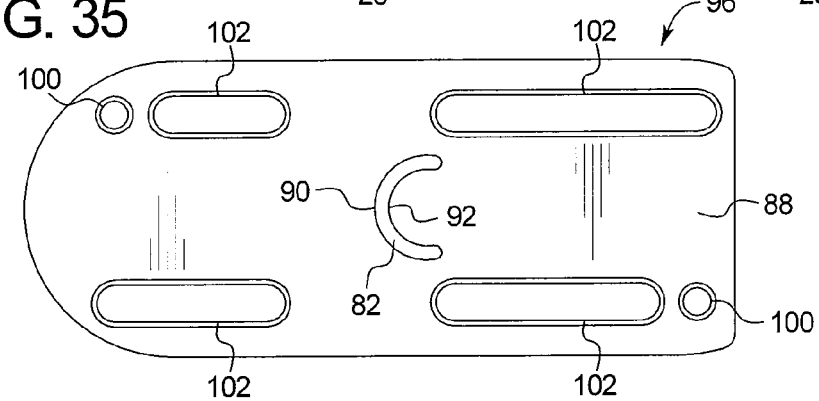
FIG. 35 is a top view of the second housing.

As shown in FIGS. 27 and 35, the housing 16 may be provided with a bottom recess 82 that receives the first side 84 of the blade 28 facing the first opening 12 and the second side 86 of the blade 28 facing the second opening 18. This is helpful to provide a cleaner cut through the catheter by supporting the bottom surface of the catheter directly adjacent the blade 28. Thus, the recess 82 extends downward from a support surface 88 that the bottom of the catheter rests on. For example, in the embodiment of FIGS. 24-36, where the catheter shape is a D-shaped, the support surface 88 is flat to support the flat side of the D-shaped catheter. However, the support surface 88 generally matches the outer shape of the catheter and could be round if the catheter is round, etc. In the embodiment of FIGS. 24-36, where the blade 28 is curvilinear, the recess 82 may have a convex side 90 that wraps around the outside (first side 84) of the blade 28 and a concave side 92 that reaches into and surrounds the inside (second side 86) of the blade 28. As shown in FIGS. 27-31 and 35-36, it may be particularly advantageous to make the housing 16 out of two pieces 94, 96 to simplify manufacturing of the housing 16. For example, the cutting passageway 20 may be a hole extending all the way through the first housing 94, which may be drilled or otherwise formed in the first housing 94. The blade recess 82 may then be separately formed in the second housing 96 by milling or otherwise forming the recess 82 in the second housing 96. Where the catheter shape is non-round, the two-piece housing 94, 96 may also make it easier to form the passageways for the catheter. For example, where the catheter is D-shaped, the top surface 88 of the second housing 96 may be flat to form the bottom of the passageways 14, 64, while the bottom of the first housing 94 may be provided with half-round channels 98A, B to form the top of the passageways 14, 64. The first and second housings 94, 96 may be provided with a plurality of tabs 100 and corresponding recesses 102 to orient the housings 94, 96 together, and adhesive may be used to secure the housings 94, 96 together.

As shown in FIGS. 25-26 and 32-34, the cutting member 24 may be connected to the knob 26 with tabs 104 and recesses 106 that receive each other. For example, the knob 26 may have a cavity 108 that receives the top of the cutting member 24, and the cavity 108 may have one or more tabs 104 that extend into the cavity 108. The cutting member 24 may have corresponding recesses 106 that receive the tabs 104 to secure the knob 26 and cutting member 24 together.

Preferably, the cavity 108 in the knob 26 is open on one side so that the top of the cutting member 24 can be slid laterally into the cavity 108 as the tabs 104 and recesses 106 receive each other.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A cutting tool for cutting a tip of a catheter, comprising:
   a housing comprising:
      a first passageway sized to accept a catheter body and a second passageway sized to accept a cutting member;
      a pair of first catches on the housing;
      a guide attached to said cutting member, said guide restraining said cutting member from rotating within said second passageway, the guide comprising:
         a central portion for retaining the cutting member, and
         a pair of second catches being provided on the guide, each of the pair of second catches being flexible and extending away from the central portion; and
      a guide passageway generally parallel to and in fluid communication with the second passageway, the pair of second catches of the guide being movable through the guide passageway as the cutting member moves through the first passageway;
   said second passageway transecting said first passageway, and said cutting member comprising an arc-shaped blade, said blade being at least as wide as said catheter body;
   wherein said catheter body is extendable through said first passageway to a position where a desired distal end of said catheter body is aligned with said second passageway, said cutting member being pushable through said second passageway until said blade crosses said first passageway, said blade thereby cutting through said catheter body to form an arc-shaped distal end on said catheter body; and
   wherein the pair of first catches engages the pair of second catches to prevent the cutting member from being removed from the second passageway.

2. The cutting tool according to claim 1, wherein said blade is convex-shaped, said distal end of said catheter body formed by said blade thereby being convex-shaped.

3. The cutting tool according to claim 1, wherein said second passageway and said cutting member comprise a round cross-section.

4. The cutting tool according to claim 3, wherein said cutting member comprises a hollow cylindrical body.

5. The cutting tool according to claim 4, wherein a first side of said hollow cylindrical body is disposed in the direction of a proximal end of said catheter body and a second side of said hollow cylindrical body is disposed in the direction of a remnant that is cut loose from said catheter body to form said convex-shaped distal end, said blade being disposed on said second side and said first side being relieved so that said first side does not contact said catheter body as said blade crosses said first passageway.

6. The cutting tool according to claim 5, wherein said blade has a blunt end.

7. The cutting tool according to claim 5, wherein said blade is relieved, a center of said blade being disposed higher than outer regions of said blade.

8. The cutting tool according to claim 3, wherein said blade comprises a bevel in a single direction along a full circumference of said hollow cylindrical body, a first side of said hollow cylindrical body is disposed in the direction of a proximal end of said catheter body and a second side of said hollow cylindrical body is disposed in the direction of a remnant that is cut loose from said catheter body to form said convex-shaped distal end, a stop preventing said first side from crossing said first passageway so that said first side does not contact said catheter body as said blade crosses said first passageway.

9. The cutting tool according to claim 8, wherein said stop is removable to allow said first side to cross said first passageway so that said first side cuts through said catheter body as said blade crosses said first passageway, said distal end of said catheter body formed by said blade thereby being concave-shaped.

10. The cutting tool according to claim 1, wherein said cutting member comprises a knob on an end opposite from said blade, said guide being connected to said knob, and said knob being larger in size than said second passageway, said knob contacting said housing when said blade crosses said first passageway to stop the travel of said blade.

11. The cutting tool according to claim 1, wherein the cutting member comprises a knob on an end opposite from said blade, said knob being larger in size than said second passageway, and further comprising a locking member, said locking member being disposed between said knob and said housing and preventing said blade from crossing said first passageway until said locking member is removed.

12. The cutting tool according to claim 1, wherein said first passageway comprises a first opening and a second opening, said first and second openings being out of alignment with each other, said catheter body being bent within said first passageway to frictionally restrain said catheter body within said first passageway.

13. The cutting tool according to claim 12, wherein said first passageway is curved from said first opening to said second passageway, and said first passageway is straight between said second passageway and said second opening, said second opening adapted to receive a remnant that is cut loose from said catheter body to form said arc-shaped distal end.

14. The cutting tool according to claim 1, in combination with a dual lumen catheter, said dual lumen catheter comprising a catheter body with a septum separating an interior of said catheter body into two side-by-side lumens, an exterior of said catheter body comprising a mark in alignment with said septum, wherein said blade is convex-shaped, said distal end of said catheter body formed by said blade thereby being convex-shaped, and said catheter body is visually alignable relative to said cutting member so that a center of said convex-shaped blade cuts along said septum.

15. The cutting tool according to claim 14, wherein said exterior of said catheter body comprises a plurality of equally spaced apart marks, each of said marks comprising a longitudinal mark identifying said septum and a lateral mark identifying different cutting lengths.

16. The cutting tool according to claim 1, wherein said housing further comprises a third passageway sized to accept a catheter body, said second passageway transecting only a portion of said third passageway, wherein said catheter body is extendable through said third passageway to a position where a desired side port is aligned with said second passageway, said cutting member being pushable through said second passageway until said blade crosses said third passageway, said blade thereby cutting through a side portion of said catheter body to form a side port on said catheter body.

17. The cutting tool according to claim 1, wherein said first passageway comprises a D-shaped cross-section sized to accept a D-shaped catheter body.

18. The cutting tool according to claim 1, wherein said blade is convex-shaped, said distal end of said catheter body formed by said blade thereby being convex-shaped, further comprising a guide attached to said cutting member, said guide restraining said cutting member from rotating within said second passageway, said second passageway and said cutting member comprise a round cross-section, said cutting member comprises a hollow cylindrical body, a first side of said hollow cylindrical body is disposed in the direction of a proximal end of said catheter body and a second side of said hollow cylindrical body is disposed in the direction of a remnant that is cut loose from said catheter body to form said convex-shaped distal end, said cutting blade being disposed on said second side and said first side being relieved so that said first side does not contact said catheter body as said blade crosses said first passageway, and said cutting member comprises a knob on an end opposite from said blade, said knob being larger in size than said second passageway, and said knob contacting said housing when said blade crosses said first passageway to stop the travel of said blade.

19. The cutting tool according to claim 1, wherein said first passageway comprises a support surface supporting said catheter body on an opposite side from an initial position of said blade, said housing comprises a blade recess extending from said support surface, said blade recess receiving said blade after said blade crosses said first passageway, and said blade recess has a concave side with said support surface surrounding an inside of said arc-shaped blade and being directly adjacent said inside of said blade.

* * * * *